United States Patent [19]

Aoshima

[11] Patent Number: 5,013,380
[45] Date of Patent: May 7, 1991

[54] PROCESS FOR PRODUCING INTEGRATED STRUCTURES OF SYNTHETIC CORUNDUM SINGLE-CRYSTALS

[76] Inventor: Hiroaki Aoshima, 4-34-14 Yayoicho, Nakano ku, Tokyo, Japan

[21] Appl. No.: 373,868

[22] Filed: Jun. 29, 1989

[30] Foreign Application Priority Data

Jul. 4, 1988 [JP] Japan .................................. 63-167262

[51] Int. Cl.$^5$ .............................................. B32B 31/18
[52] U.S. Cl. .................................. 156/250; 156/256; 156/264
[58] Field of Search ................ 156/89, 250, 256, 264, 156/254, 608, 620.1, 629, 633, 645; 350/162.11, 162.16, 162.17, 320

[56] References Cited

U.S. PATENT DOCUMENTS

3,235,428 2/1966 Naymik ................................. 156/250
3,964,942 6/1976 Berkenblit et al. .................. 156/647
4,671,846 6/1987 Shimbo et al. ...................... 156/153

Primary Examiner—Caleb Weston
Attorney, Agent, or Firm—David O'Reilly

[57] ABSTRACT

In a process for producing an integrated structure of synthetic corundum single crystals, which is disclosed herein, a synthetic corundum single-crystal ingot is cut to form a first rectangular prism, and one face of the first rectangular prism is optically polished to form a second rectangular prism. Then, the second rectangular prism is cut, along a plane perpendicular to the optically polished face, into a first plate piece which is then surrounded with a jig, and upper and lower surfaces thereof are optically polished to form a second plate piece. The second plate pieces are put one on another with their plane, edges, axes and axial angles of the upper and lower optically-polished faces being aligned with one another, respectively by use of an incorporating jig. The superposed plate pieces are brought into chemical contact with one another and heated at a temperature lower than a melting point of the synthetic corundum, whereby they are closely joined or bonded.

9 Claims, 6 Drawing Sheets

PROCESS FOR PRODUCING INTEGRATED STRUCTURES OF SYNTHETIC CORUNDUM SINGLE-CRYSTALS

BACKGROUND OF THE INVENTION

1. Field of the Invention

The present invention relates to a process for producing an integrated and assimilated structure of synthetic corundum single-crystals which is used as an ornamental article, a scientific appliance, an industrial instrument or the like and which is made by putting a plurality of single crystal plates of synthetic corundum one on another and chemically bonding them.

2. Description of the Prior Art

Synthetic corundums such as sapphire have been conventionally used for a spectroscopical container (cell) for optical transmission samples because of the excellent optical wavelength transmission characteristics and their excellent resistances to chemicals and recently, they are being also used for a superconductive container because of their larger thermal conductivities.

Figures 14A, 14B, 15A, 15B:
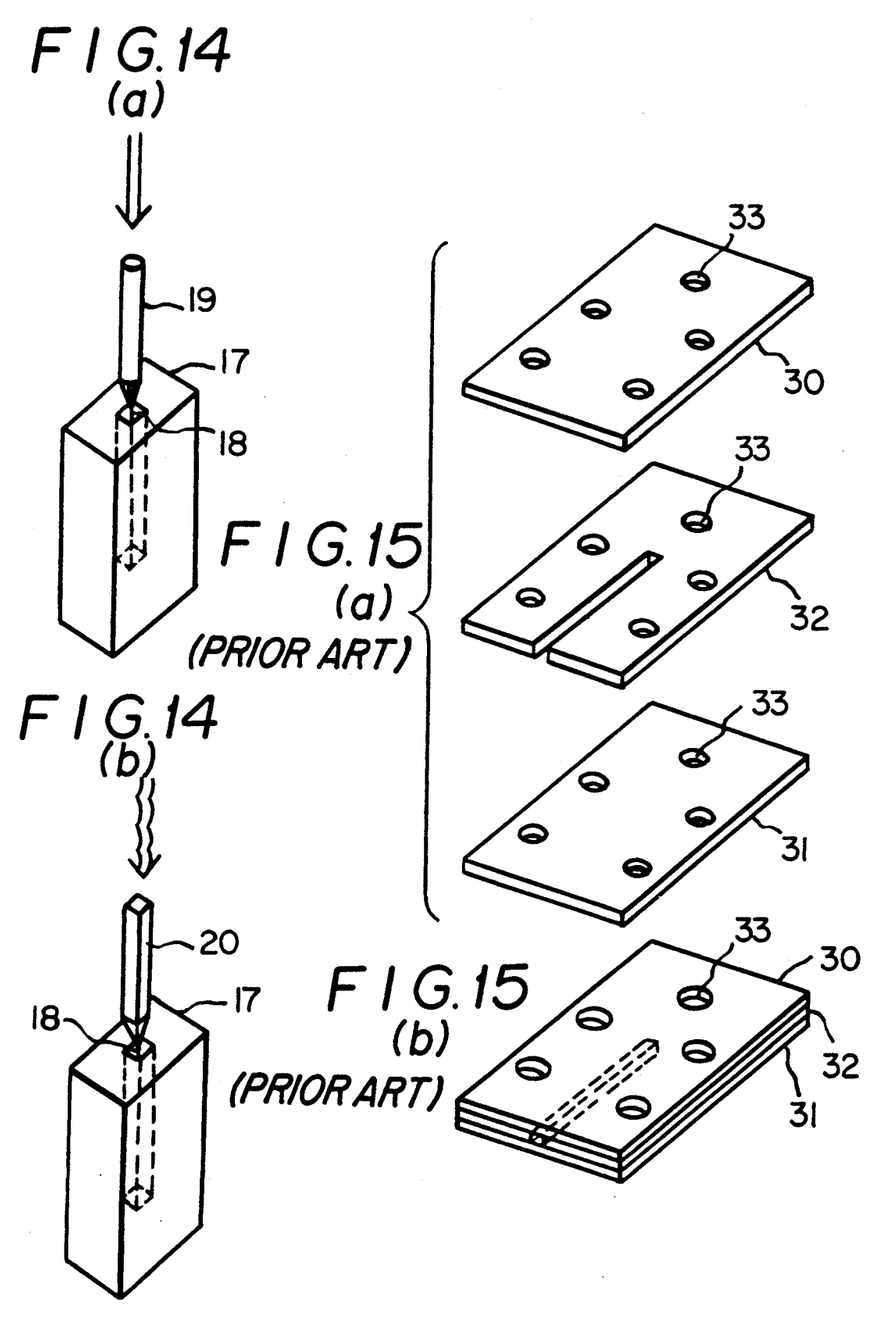

One example of a process for producing such a cell is shown in FIG. 15. In this process, as shown in FIG. 15(a), is recessed plate 32 made of teflon is interposed as a packing between two corundum window plates 30 and 31 into a state shown in FIG. 15(b), and bolts and nuts are inserted into through-holes 33 penetrating the corundum window plates 30 and 31 and the recessed plate 32 and tightened to form the cell.

In such a method, however, if the bolts are too tight, schlierens and strains may be produced, or even if optical wavelength transmission characteristics available for a spectroscopic container or cell are satisfactory, the respect of a resistance to chemicals is unsatisfactory. More specifically, a solution may be gradually penetrated between the plate and the teflon packing, but such method had to be used from necessity. On the other hand, with the super-conductive cell, there is a difference in coefficient of thermal expansion between the corundum window plate and the teflon packing due to their resistance to freezing, pressure and heat and hence, not only this cell is not fit for use, but also, it is very dangerous.

In addition, in making a thin super-conductive film, a substrate must be fit for use in a normal CVD process even at temperatures more than 900° C., and less than 268.9° C.

A microminiature material capable of measuring a ultra-amount super-precisely and super-correctly and having characteristics of resistance to freezing, heat, pressure and chemicals is only a single crystal of synthetic corundum (e.g., sapphire) ranking in hardness next to diamond having the highest hardness on the earth. Except for the requirement of the above resistances, however, if a material is amorphous, such materials, even if they are homogeneous, can be affixed to each other because they have no anisotropy. On the other hand, it is impossible to affix single crystals having an anisotropy such as synthetic corundum in view of their crystallographic structures. On the consideration that such affixing is contrary to solid physics and out of the bounds of possibility, the experiments and studies therefor have been not made, and even similar examples cannot be found.

In the regard to the aforesaid optical polishing, the polished face will now be described. The polished face is a flat face of a wavelength order and has a flatness accuracy $\lambda/8$ or less of red ray wavelength ($\lambda = 6328 \text{Å}$) as measured by HeNe laser interference flatness-measuring device.

In the conventional boring method using a ultrasonic machine, it is technically and technologically very difficult to bore a rectangular hole in a rectangular prism and further to polish the inner surface of the rectangular hole, and hence, it requires a great deal of skill to do so. If a rectangular through hole is made by boring, however, it is possible to polish the inner surface of the through hole. If the boring operation is discontinued in the middle to provide a rectangular hole rather than a rectangular through hole, it is impossible to polish the inner surface thereof. Therefore, the conventional cell of synthetic corundum is a non-bottomed flow cell and hence, in a case bottom is necessary, a plug must be mounted. This is the case of a cylinder having a rectangular through hole to the end, rather than the case of a bottomed container.

In addition, if a rectnagulr hole is bored to provide a container, the inner surface of that rectangular hole cannot be polished with optically high accuracy.

As described above, it is impossible to produce an integrated optically measuring container from single crystals of synthetic corundum through a boring method.

SUMMARY OF THE INVENTION

It is an object of the present invention to provide a process for producing an integrated optically measuring container by putting a plurality of single crystals of sythetic corundum one on another and joining or bonding them, which container has resistance to chemicals, heat, pressure and freezing (cooling), and in which the above problems can be overcome.

To attain the above object, according to the present invention, there is provide an integrated process for producing a structure of synthetic corundum single-crystals, comprising the steps of cutting synthetic corundum single-crystal ingot to form a first rectangular prism 1, optically polishing one face of the first rectangular prism 1 to form a second rectangular prism 2, surrounding the second rectangular prism 2 with a jig and cutting the second rectangular prism 2 into a first plate piece 6 along a plane perpendicular to the optically polished face, optically polishing upper and lower surfaces of the first plate piece to form a second plate piece 7. The second plate pieces 7 are then put one on another with their plane, edges, axes and axial angles of the upper and lower optically-polished faces being aligned with each other, respectively by use of an assembling jig, bringing them into chemical contact with one another, and heating the adhered pieces at a temperature lower than the melting point of the synthetic corundum to closely join or bond them.

In addition, there is provided a process for producing an integrated structure of synthetic corundum single-crystals comprising the steps of cutting a synthetic corundum single-crystal ingot(s) to form a first rectangular prism 1, optically polishing one face of the first rectangular prism 1 to form a second rectangular prism 2, surrounding the second rectangular prism 2 with a jig and cutting the second rectangular prism 2 into a first plate piece 6 along a plane perpendicular to the optically polished face, optically polishing upper and lower surfaces thereof to form a second plate piece then, cutting the second plate piece 7 into cut plate pieces 8. The cut plate pieces 8, are separated and a plurality of the separated cut plate pieces 8 are put one on another with their plane, edges, axes and axial angles being aligned with each other, respectively, by use of an assembling jig so that the respective optically-polished faces on the upper and lower opposed surfaces may be closely mated with each other, bringing them into chemical contact and heating the contacted pieces at a temperature lower than a melting point of the synthetic corundum.

Further, there is provided a process for producing an integrated structure of synthetic corundum single-crystals wherein after a cut is made in the second plate piece 7 to be cut into the cut plate pieces up to the middle thereof before the second plate piece 7 having the upper and lower surfaces optically polished is cut into the cut plate pieces 8, the aforesaid cutting is effected to form a plurality of cut plate pieces 8 and a single grooved plate piece 9 and to separate them. The grooved plate piece 9 is inserted between the cut plate pieces 8, thereby integrating and assimilating them by the aforesaid closely joining step of heating.

In the above processes, the optically polished faces are put one on another with their planes, edges, axes and axial angles being aligned with each other, respectively, and are integrated by use of chemical bonding or interfacial reaction and heating. Therefore, it is possible to produce an integrated optically measuring container which has been conventionally incapable of being produced which is excellent in resistance to chemicals, heat, pressure and freezing (cooling) and hence, is a chemically and physically optimal cell. In addition to such a container, it is possible to provide an article physically resistance to heat chemically resistant to chemicals and having a complicated and elaborate shape.

The above and other objects, features and advantages will become apparent from a reading of the preferred embodiments, taken in conjunction with the accompanying drawing.

BRIEF DESCRIPTION OF THE DRAWINGS

FIGS. 14(a) and (b) are illustrations for explaining fracture tests for a cell, FIG. 14(a) being an illustration for explaining a impact peel fracture test, and FIG. 14(b) being an illustration for explaining a vibration peel fracture test; and FIGS. 15(a) and (b) are views of the structure of a conventional cell, FIG. 15(a) being an exploded view of elements, and FIG. 15(b) being a perspective view of the elements overlapped.

DESCRIPTION OF THE PREFERRED EMBODIMENTS

The individual steps of the process according to the present invention will now be described.

(1) A step of processing a plurality of cut plate pieces by use for an assembling jig so that upper and lower optically polished faces are mated with each other.

The assembling jig is a plate having a single optically flat face (prototype), as measured for interference fringes of the optically polished faces.

A commonly used measurement is for a spacing between a point and a point, wherein a difference in unevenness of a line which is a continuum of points is measured.

A measurement used in the present invention is for a face, rather than a point and a line. The measurement exceedingly contemplates the reproducibility of an assembly rather than a numerical value thereof.

A face whose fringe is to be measured, for use in the present invention, is only a single face. Therefore, errors in measurement cannot be accumulated to result in an inaccuracy, as in the measurement of a plurality of faces.

(2) A step for aligning planes, edges, crystallographic axes and axial angles of the crystals.

If a crystal is cut in a variety of directions, and the resulting cut pieces are compared for hardness, resilience, and optical, thermal, electrical and magnetical properties, it can be found that these properties are different depending upon directions. It follows that "Crystal" can be defined to be "a solid having physical properties different depending upon directions".

For example, with a single crystal of $Al_2O_3$ grown in a Verneuil process, its coefficients of thermal expansion are considerably different between a direction of crystallographic axis c and a direction of crystallographic axis a.

Coefficient of thermal expansion in the direction of axis c :$67 \times 10^{-7}$ cm/° C./cm Coefficient of thermal expansion in the direction of axis a :$50 \times 10^{-7}$ cm/° C./cm Therefore, with a growing direction not determined, irregular cracks may be very often produced with shrinkage in cooling following the completion of growth of crystal due to such difference in coefficient of thermal expansion.

When the crystallographic axis c is inclined at about 60° with respect to an axis of growth, the thermal strain is smallest in the direction of growth and hence, the cranking rate in cooling is smaller. For this reason, the ingot of $Al_2O_3$ generally has the crystallographic axis c already inclined at about 60° with respect to the axis of growth. Of course, this should be confirmed. According to the present invention, in forming an ingot, only the axis of growth is decided as the direction for c', and a face perpendicular to the axis c' is a face c'. These directions and faces are reasonable and even if there are some defects in the resulting ingot, the latter is less sensitive. The selection of such direction and face even in the subsequent contacting and bonding steps is most desirable for the results of a test. If necessary, however, an axis of rotation of a crystal may be selected.

Except when the axis of growth is decided as an axis c', the processing steps according to the present invention are not concerned with crystallographic axes, axial ratios and axial angles possessed by a synthetic corundum of $Al_2O_3$, and hence, for convenience, other axes are optionally decided as axes a and b.

Figure 8A:
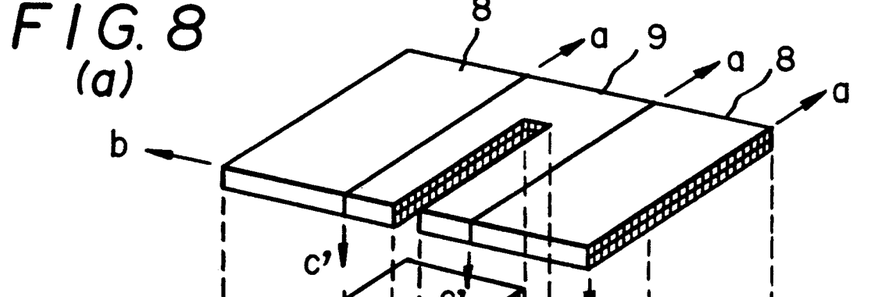
FIGS. 8(a) to (d) are illustrations for explaining a step of bringing the plate pieces into contact with one another, FIG. 8(a) illustrating the second plate piece as being cut, FIGS. 8(b) and (c) illustrating the cut pieces as being in the course of the step of contacting one another, and FIG. 8(d) being an illustration for explaining the alignment of crystallographic axes.
Figure 8B:
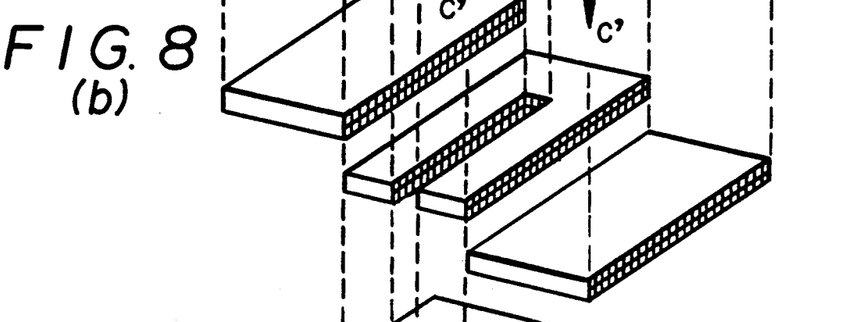
Figures 8C, 8D:
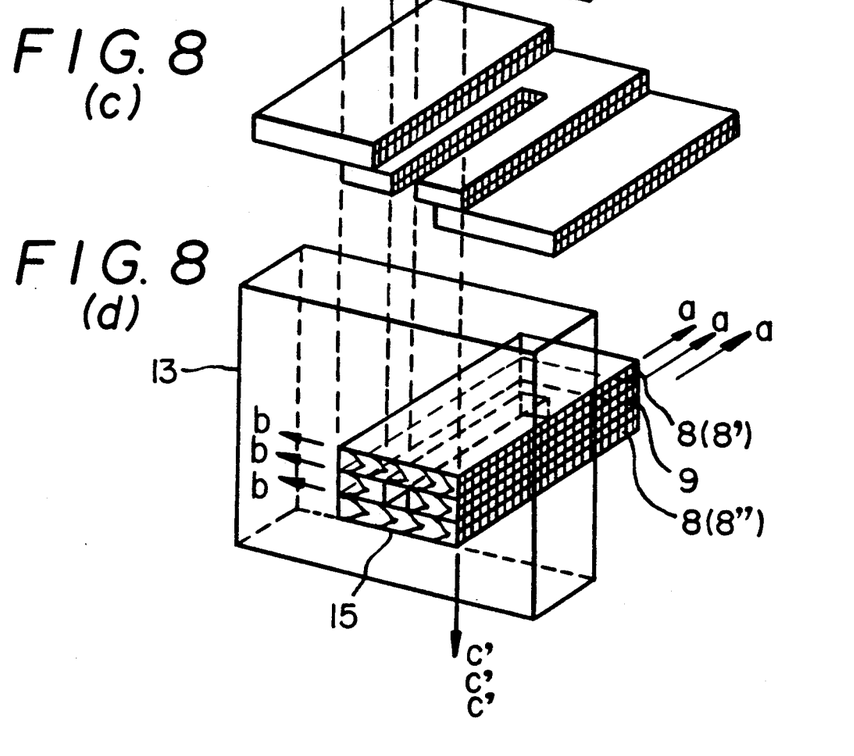

Thereupon, an upper plate piece 8', a grooved plate piece 9 and a lower plate piece 8" resulting from equal division of a single simple-plate along a plane including axes a and c' as shown in FIG. 8(a) are put one on another into three layers as shown in FIGS. 8(b) and (c), and using an interference-fringe reference-face measurement, they are aligned with one another so as to be parallel to the individual axes a and vertical to the individual axes b, with the face c' being the boundary faces and with individual faces A (which is a face parallel to the axis a) in the three layers of the upper plate peice 8', the grooved plate piece 9 and the lower plate piece 8" being the interference fringe measuring faces of the optically polished faces.

(3) A putting step
Interference-fringe reference-face measurement

Figure 6:
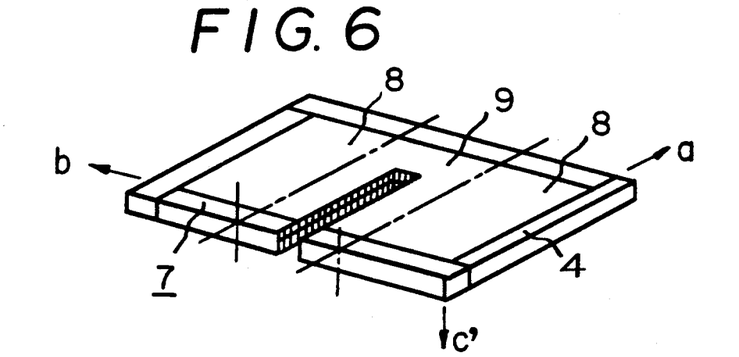
FIG. 6 is a view of the second plate piece for explaining the division thereof.

The single simple-plate (a cell plate (second plate piece 7); see FIG. 6) having the optically polished faces already observed for the interference fringes with the optically flat prototype 13 applied thereto is equally divided into three plate pieces which are then put one on another into three layers with their optically polished faces being in the same direction (see FIG. 8). The optically flat prototype 13 is applied to the optically polished faces of the three layers to equalize their interference fringes 15 with an interference fringe 14 of the optically polished face (see FIG. 7) of the single cell plate 7 which is still not divided into three portions, thus reproducing the optically polished faces.

If such measurement is used, it is possible to compare the interference fringes 14 and 15 before and after cutting, on a single optically polished face, and to reproduce equivalent faces. If such a way is applied to a processing of a single crystal, the crystallographic axes, axial ratios and axial angles of the single crystal can be reproduced so as to become identical even after they have been processed, thereby allowing the single crystals to be put one on another.

(4) A chemically contacting step

A humidity, temperature and air-cleaned controlled box is used

In order to put a plurality of single crystals of synthetic corundum one on another to closely contact them, it is an important essential point to make an environment therefor.

Conditions for such an environment result from experiments of trial and error, and if even one of the conditions is lacking the joining is impossible.

The environmental conditions include:
(1) cleanliness;
(2) constant humidity during operation, 80±5%;
(3) constant temperature during operation, 28±2° C.; and
(4) ionized air well-balanced positively and negatively being constantly produced by corns discharge.

In a working space having environmental conditions as described above (which is a box or a comparted plate and which is herein referred to as a humidity, temperature and air-cleaned controlled box), faces c', i.e., optically polished faces to be superposed into three layers, of an upper plate piece 8', a grooved plate piece 9 and a lower plate piece 8" resulting from division of a single simple-plate into three portions as shown in FIG. 8 are cleaned several times alternately with an inorganic solvent and an organic solvent with careful attention paid, so that dust or the like will not enter the interfaces between faces of axes c' at all when they are superposed. Finally, the individual faces c' are once more slowly and carefully wiped up with a thinner (an organic solvent). In this case, it is believed that the optically polished faces are cooled for a moment due to evaporation of the organic solvent, and during this time, hydrogen and oxygen atoms within the enviroment are adsorbed onto the optically polished faces and act as catalysts in the interfaces to maintain the contact of the faces c' (optically polished faces).

(5) A step of heating at a temperature lower than melting point.

The synthetic corundum $Al_2O_3$ has a melting point of 2030° C. The heating is effected at 1200° C. lower than this melting point during the contacting step.

The synthetic corundum is a single crystal having a crystallographic structure and hence, the upper plate piece 8', the grooved plate piece 9 and the lower plate piece 8" resulting from division of a single simple-plate into three portions (see FIG. 8) have the same axes, the same axial ratios and the same axial angles, and each of them is a single crystal independently having a crystallographic structure. Therefore, in order to bring the single crystals into contact with one another to join them, thereby providing an integrated uniform single crystal, the respective crystallographic axes, axial ratios and axial angles of the face c', i.e., the optically polished faces must be correctly aligned with one another, respectively, and they must be heated at a proper temperature with their contact being uniformly maintained. In the heating, if they are locally heated, the boundary faces uniformly contacted may be released at a moment due to differences in thermal expansion caused by differences in heated temperatures. Accordingly, what is important is a control of temperature until the contacted faces are joined and integrated without damaging of the optically polished faces, such as to raise the temperature from ambient temperature in a temperature gradient. It is believed that the boundary face has a considerably distorted atomic arrangement remarkably different from the internal structure of the single crystal due to the external influence exerted by the optical polishing.

Figure 10:
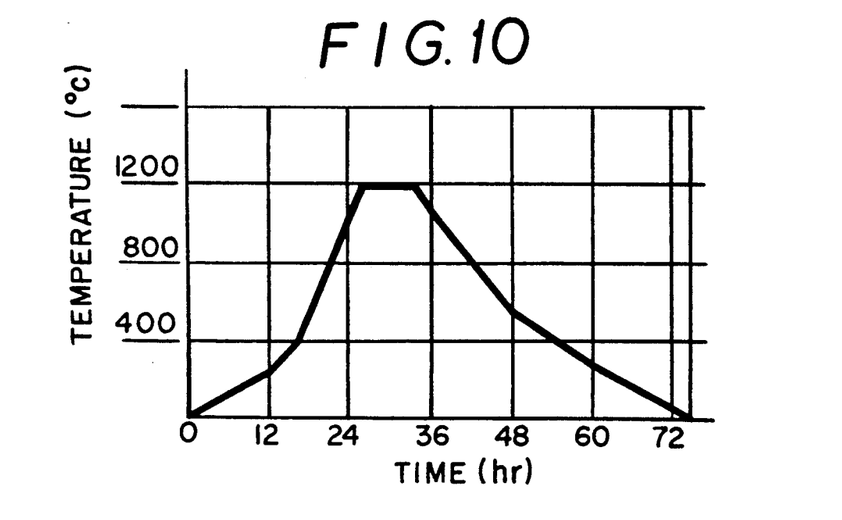
FIG. 10 is a graph illustrating a temperature profile for heating.

Such a state is very instable and hence, if the temperature is gradually raised, various crystallographic structures may be varied on the boundary face, and in the interface between two layers, the chemical bonding tends to easily take place. A temperature gradient where such chemical bonding easily takes place is as shown in FIG. 10.

(6) A heating and contact-joining step

It is believed that the contact-joining by heating is a chemical bonding by an interfacial reaction.

It is surmised that the crystallographic structures of the optically polished faces of the single crystals to be chemically bonded have different arrangements of atoms. The synthetic corundum $Al_2O_3$ includes ion bonds having a covalent linkage and hence, the optically polished face is in a state where a chemical bonding power acting on and between particles such as atoms and ions is cut off. Therefore, the atoms and ions on such a face have joinable bonds still left thereon, so that a chemical reaction is apt to take place on that face, and if even a surface of a crystal made in vacuum is exposed to air, hydrogen, oxygen and the like in the air is absorbed onto the crystal surface at a moment. Such molecules are disassociated on the surface into hydrogen and oxygen atoms which form chemical bonds together with the joinable bonds of the atoms on the surface.

Still more, the optically polished face externally influenced is in a very instable state, and in order to chemically bond such faces to each other, they may be heated with the temperature gradually raised from ambient temperature, so that the interface may be active with the molecule of hydrogen and oxygen thereon acting as a catalyst, whereby a chemical reaction takes place causing the crystallographic structure of the interface to chemically change slowly. Thereupon, the temperature is gradually returned down to ambient temperature, whereby the active state rests, allowing chemical bonding, whereby the optically polished faces are joined together.

(7) A particular producing process
A process for producing a container
This process comprises the steps of dividing a simpleplate of a sythetic corundum single crystal into three pieces; an upper plate piece 8', a grooved plate piece 9 and a lower plate piece 89" (see FIG. 8), putting the three pieces one on another, closely contacting them, heating them at a temperature lower than a melting point to joining them, thus providing an optically measuring container.

Specified examples will be described below in detail with reference to the accompanying drawings.

A single crystal of synthetic corundum $Al_2O_3$ is a hexagonal system face-centered diamond structure lattice, and the aligning step described in the item (2) is not concerned with the crystallographic axes, axial ratios and axial angles possessed by the synthetic corundum. However, only the axis of growth of an ingot is defined as an axis c'. for convenience, axes a and b are optionally defined, and description will be made on the assumption that axial ratios $a \neq b \neq c'$ and axial angles $\alpha = \beta = \gamma = 90°$.

Figure 1:
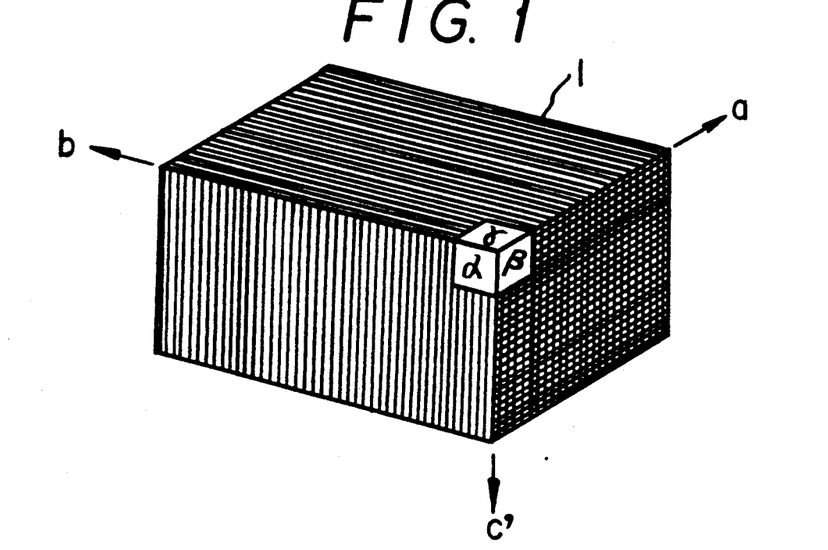
FIG. 1 is a view of a formed ingot.

FIG. 1 illustrates a first rectangular prism 1 having axes a, b and c', axial ratio $a \neq b \neq c'$ and axial angles $\alpha = \beta = \gamma = 90°$ ($\pm < 2$ minutes or less) and formed from processing of an ingot of synthetic corundum.

Figure 2:
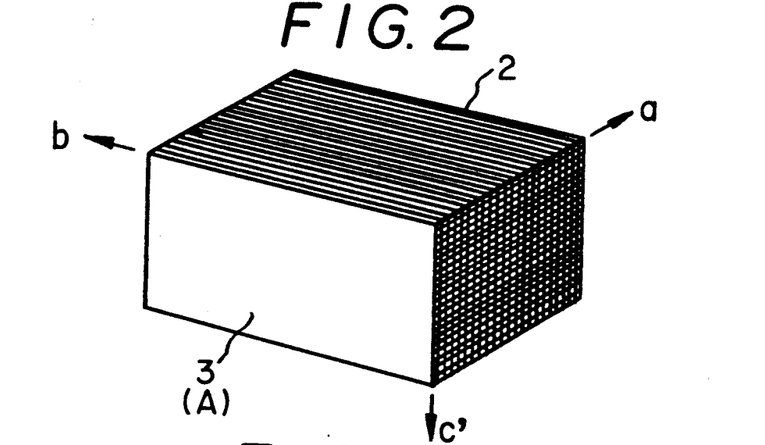
FIG. 2 is a view of a second rectangular prism for explaining the measurement of an interference fringe reference face.

FIG. 2 is a view for illustrating measurement of an interference fringe reference face as described in the item (1), wherein only a face (face A) perpendicular to the axis a of the first rectangular prism 1 is optically polished with a high accuracy (a flatness $<\lambda/8$, $\lambda = 6328 Å$) to form a second rectangular prism 2. Until all the subsequent steps are completed, this face A (optically polished face) is used as a reproduceable interference fringe reference face 3 for observing and confirming the interference fringes produced together with the optically flat prototype 13 in the processing steps.

Figure 3:
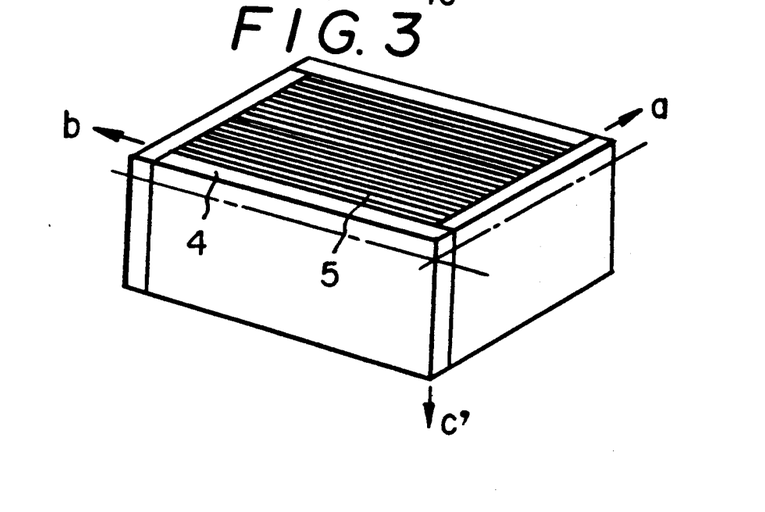
FIG. 3 is a view of a second rectangular prism to be cut.

FIG. 3 is a view of a third rectangular prism 5 which is produced from cutting of the second rectangular prism 2, by completely surrounding and covering the periphery of the second rectangular prism 2 in a box-like manner with an optically polisher 4 made of the same material as the synthetic corundum and similar in crystallographic axes, axial ratios and axial angles (but different in hardness depending upon axial directions) and securing it with an adhesive.

This third rectangular prism 5 is cut along a plane parallel to the axes a and b into a predetermined thickness.

Figure 4:
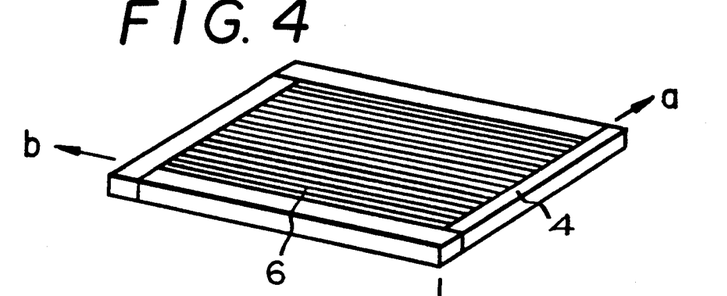
FIG. 4 is a view of a first plate piece immediately after the second prism is cut.

FIG. 4 illustrates the shape of the first plate piece 6 immediately after cutting of the prism shown in FIG. 3.

Figure 5:
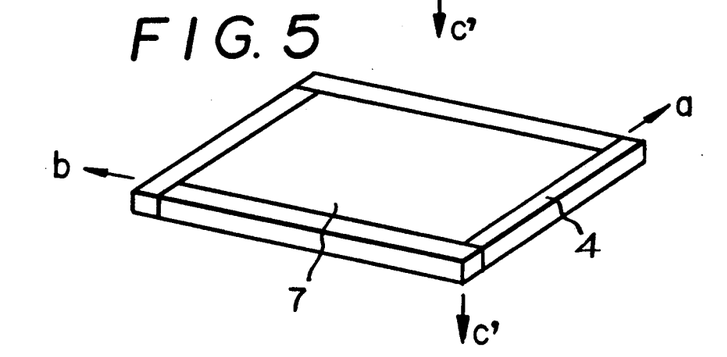
FIG. 5 is a view of a second plate piece immediately after the first plate piece is optically polished.

FIG. 5 illustrates the shape of a second plate piece 7 immediately after polishing. The first plate piece 6 is optically polished by use of both of a double-polishing machine and an oscillated automatic polishing machine with a high accuracy (flatness $<\lambda/8$, parallelism $\pm <0.5$ seconds and the measurement being made with the interference fringes on the face and back brought into one color by an interferometer), thereby providing the second plate piece 7.

FIG. 6 illustrates the second plate piece 7 being divided. Prior to division, the central portion of the second plate piece 7 is grooved in a direction of the axis a by an automatic cutter. This grooving allows a concave groove to be formed by stopping the cutter during cutting. The width of the groove is about 50 u (microns) or more depending upon the thickness of a diamond cutting edge, and the depth of the groove depends upon the point of time at which the cutting is stopped.

After grooving, the second plate piece 7 is equally cut into three portions along lines parallel to the axis a and perpendicular to the axis b, and the optical polisher 4 is removed, thus forming two cut plate piece portions 8 and 8 and one grooved plate piece portion 9. The two cut plate piece portions 8 and 8 are used as an upper plate portion 8' and a lower plate portion 8", respectively.

Figure 7:
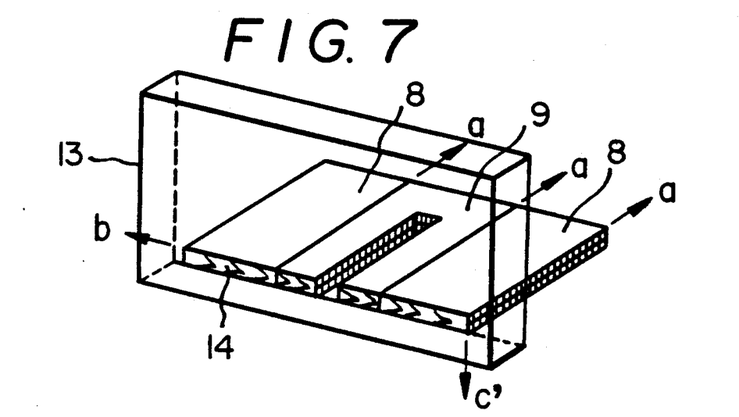
FIG. 7 is a view of optically polished faces as being in an intermediate examination.

FIG. 7 illustrates the optically polished faces as being subjected to an intermediate examination, wherein the portions on the opposite side of the optical flat prototype 13 (transparent glass plate) are shown by a solid line for the purpose of avoid complicating the drawing. If the optical flat prototype 13 is applied to the interference fringe reference faces 3, i.e., the respective faces A of the upper plate 8', the grooved plate piece 9 and the lower plate 8" to observe the fringes 14, it is possible even after processing to confirm the reproduction of the same interference fringes as the second rectangular prism 2 after processing, wherein the axes a and b are also in the same directions as those before processing.

FIGS. 8(a) to (d) are illustrations for explaining the step for contacting the three portions, wherein FIG. 8(a) is a cutting diagram, FIGS. 8(b) and (c) are diagrams of the three portions in the courses of the contacting step, and FIG. 8(d) is a diagram of the three portions located so that their crystallographic axes may be aligned. In FIG. 8(d), the portions on the opposite side of the optically flat prototype 13 are shown by a solid line for the purpose of avoiding complicating the drawing. In this step, the upper plate 8', the grooved plate piece 9 and the lower plate 8" are placed into a humidity and temperature air-cleaned controlled box so that they may be become uppermost, intermediate and lowermost layers, respectively. The individual faces are cleaned alternately with an inorganic solvent and an organic solvent, and the faces c' (faces perpendicular to the axis c') of the uppermost plate 8', the grooved plate piece 9 and the lowermost plate 8" are put one another in such a cleaned state so that no foreign matter such as dust can enter between the respective boundary faces, i.e., the face c'. In this case, the optically flat prototype 13 is applied to the interference fringe reference faces 3, i.e., the faces A to observe the interference fringes 15 and to reproduce fringes so that they may become the interference fringes 14 shown in FIG. 7. Thereafter, the faces c' which are the boundary faces of the upper plate 8', the grooved plate piece 9 and the lower plate 8" are brought into close contact with one another and then, they are heated to a temperature lower than the melting point of the synthetic corundum and thus chemically bonded.

Figure 9:
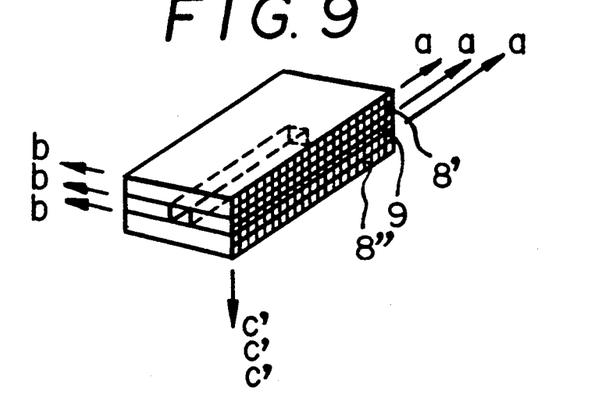
FIG. 9 is a perspective view of a container.

FIG. 9 is a perspective view of a container made from upper plate 8', the grooved plate piece 9 and the lower plate 8" which have been integrated by completely close contact with one another.

FIG. 10 is a graph illustrating a temperature profile for the heating step. This temperature profile shows the heating and clooing gradients provided when the upper plate 8', the grooved plate piece 9 and the lower plate 8" are integrated in the heating, closely contacting and joining steps described in item (6). They heated in an automatically temperature-controlled electric oven to a temperature of 1,200° C., about one half lower than the melting point, 2,030° C. of a single crystal of synthetic corundum, after being placed into a vessel made of a polycrystalline Al$_2$O$_3$ of the same material, which vessel is then covered with a lid having the same thickness as the peripheral wall thereof, so that the temperature of the entire vessel may be gradually raised uniformly.

Figure 11:
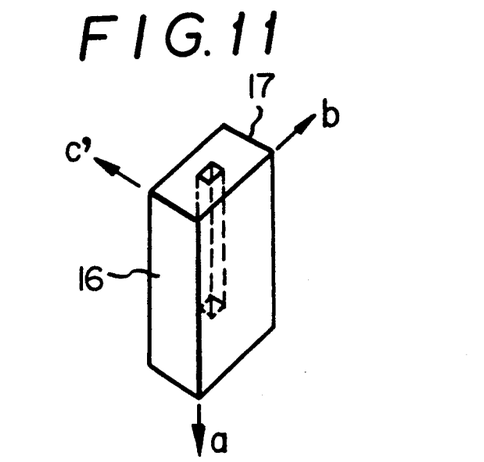
FIG. 11 is a perspective view of a cell.

FIG. 11 is a perspective view of a completed cell 17. After slow cooling, the vessel is removed from the electric automatically temperature-controlled oven, and the upper plate 8', the grooved plate piece 9 and the lower plate 8" are removed outside and observed for the interfaces by a zoom microscope (60 an d330 magnification), for the optically polished faces by an interferometer and for the thermal strains by a polarizer. After completion of the examination, the b faces 16 and 16 on the opposite sides and perpendicular to the axis b are polished.

In this manner, the upper plate 8', the grooved plate piece 9 and the lower plate 8" are completely integrated rather than being merely closely contacted, thus completing a cell 17 made of a single crystal of synthetic corundum and having optically transmittable faces optically polished with a high accuracy and free of interfaces on the bonded boundaries.

Figure 12A:
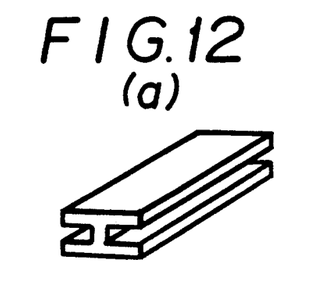
FIG. 12(a) to (d) are illustrations of applications of profiles, FIG. 12(a) illustrating an H-shaped application, FIG. 12(b) illustrating a Y-shaped application, FIG. 12(c) illustrating a U-shaped application, and FIG. 12(d) illustrating a cross-shaped application.
Figure 12B:
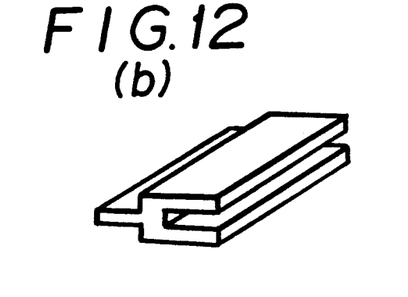
Figure 12C:
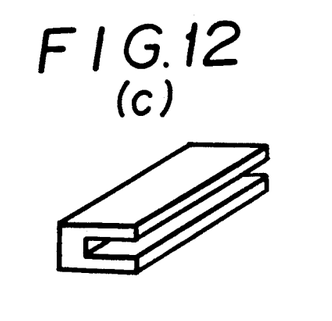
Figure 12D:
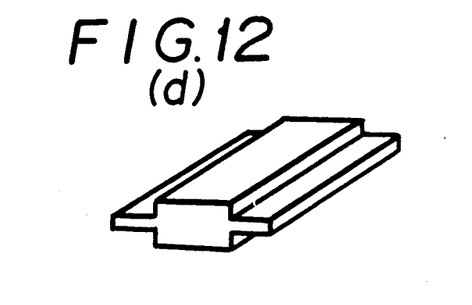

FIGS. 12(a) to (d) illustrate examples of profiles formed by application of the above-described processing method, FIG. 12(a) illustrating a product having an H-shaped section, FIG. 12(b) illustrating a product having a Y-shaped section, FIG. 12(c) illustrating a product having U-shaped section, and FIG. 12(d) illustrating a product having a cross-shaped section, wherein in any of them, the joined faces are formed by the above-described procedure.

Figure 13A:
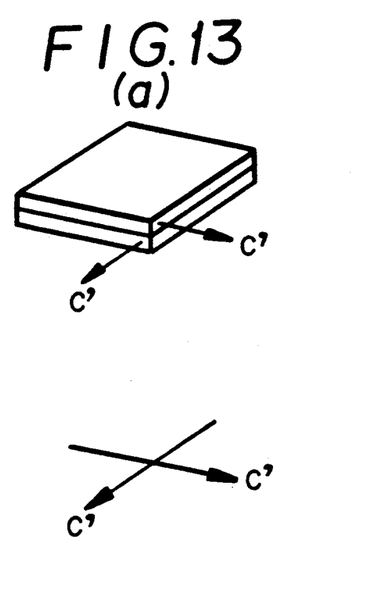
FIGS. 13(a) and (b) are illustrations for explaining an experiment for comparison of anisotropy of crystallographic axes.
Figure 13B:
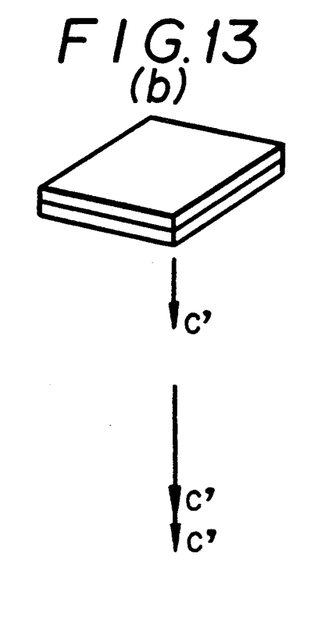

FIGS. 13(a) and (b) are illustrations for explaining examples of experiments for comparison of anisotropies of crystallographic axes. Opposite faces of a single c'-face simple plate (having dimensions of 2"×1"×1/10"), which has been made by cutting away a single crystal ingot of a single synthetic corundum having a c' axis as a axis of growth in a direction perpendicular to the axis of growth, are optically polished with a high accuracy (with a flatness of λ/8, λ=6328<, and parallelism <0.5 sec.). The c' face simple plate is cut into an R set (shown in FIG. 13(b)) of two portions which are then put onto each other so that their c' axes may be aligned with each other.

On the other hand, an ingot likewise resulting from growth with the c' axis as an axis of growth is cut through in parallel to the axis of growth and subjected to the same processing into the same size to give an L set (shown in FIG. 13(a)) of two portions which are then put onto each other with the c' axes crossed with each other.

Using the process according to the present invention, the two sets (the R and L sets) of the cut portions were brought into close contact with each other and subjected together to heating and cooling according to the temperature profile shown in FIG. 10.

As a result, the boundary faces of the L set closely contacted were completely peeled off into the original two-part state before close contact.

The visual observation showed that the boundary faces of the R set close contacted were free of any turbidity and completely transparent.

The similar observation by a zoom microscope showed that is was impossible even to adjust the focuses of the boundary faces on the microscope. In other words, there were no boundary faces.

In the above manner, the above-described clause "the crystal is a solid different in physical properties depending upon directions" was demonstrated.

The following is a description of a test of the cell 17 made by the above procedure.

(1) Physical, chemical and durability test

| Resistances to: | Temperature (°C.) | Time (hr.) | Result | Note |
|---|---|---|---|---|
| Heat | 1,600 | 6 | no change | |
| Freeze (cooling) | −268.9 | 6 | no change | |
| Chemicals | Ambient temperature | 60 | no change | Hydrogen flouride thrown in |

(2) Examination for crystallographic structure and difference in crystallographic axes The measurement of the opposite optically transmittable path surfaces by an X-ray spectrometer showed that both the opposite faces were coaxial, and no change in measurement was observed.

(3) Examination for optical strains

A visual observation using a polarizer plate showed that no strain was observed.

(4) impact peel fracture test

FIG. 14(a) is a view for explaining the impact peel fracture test for examining the joined or bonded state of the cell 17. In this test, a conical tip of a round iron rod 19 having a diameter larger than the length of a side of a square bore 18 in the cell 17 is forced into the bore 18, and the other end of the round rod 19 is strongly struck. As a result, the upper peripheral wall of the square bore 18 was finely broken into about 1×1 mm square fragments, but peeling from the jointed or bonded faces (interfaces) was not observed at all.

FIG. 14(b) is also a view for explaining a vibration peel fracture test. In this test, a pyramid-shaped tip of a square super-hard alloy rod 20 having a side length larger than the length of the side of a square bore 18 in the cell 17 was inserted into the bore 18, and the cell was subjected to a boring in an ultrasonic machine with abrasive grains being spread. After a lapse of several ours, the section of the square bore was widened, but peeling from the interface was not observed at all.

What is claimed is:

1. A process for producing an integrated structure of synthetic corundum single-crystals comprising:
    cutting a synthetic single-crystal ingot to form a rectangular prism;
    optically polishing one face of said rectangular prism;
    surrounding said rectangular prism with a jig in a clean-air environment having a predetermined controlled temperature and humidity;
    cutting said rectangular prism into a first plate piece along a plane perpendicular to said optically polished face;
    optically polishing upper and lower plane surfaces of said first plate piece;
    cutting said first plate piece into a plurality of plate pieces;
    placing said plurality of plate pieces one on top of the other with their optically polished surfaces in contact, said plurality of plate pieces having their planes, edges, axes and axial angles aligned with each other and held in an assembling jig;
    bringing said plurality of plate pieces into chemically mating contact with one another; and
    heating said mated plurality of plate pieces to a temperature substantially less than the melting point temperature of said synthetic corundum;
    whereby said plurality of plate pieces are bonded and closely joined.

2. The process according to claim 1 in which said first plate piece is cut into three pieces; said three pieces being brought into contact and mated to form a Y shape.

3. The process according to claim 1 in which said first plate piece is cut into three pieces; said three pieces being brought into contact and mated to form a U shape.

4. The process according to claim 1 in which said first plate piece is cut into three pieces; said three pieces being brought into contact and mated to form an X shape.

5. The process according to claim 1 in which said first plate piece is cut into three plate pieces equal in size.

6. The process according to claim 5 in which a notch is made in one of said three plate pieces approximately half-way; said notched plate piece being placed between the other plate pieces; whereby said three plate pieces form a container.

7. The process according to claim 1 in which said plurality of mated plate pieces are heated to a temperature of approximately 1200° C.

8. The process according to claim 7 in which said plurality of mated plate pieces are gradually heated up to the 1200' C. temperature over a temperature gradient; said temperature gradient comprising; heating said plurality of mated pieces up to a temperature of approximately 1200° C. over a period of about 24 hours; holding said 1200° C. for approximately 8 to 10 hours; and cooling said plurality of noted pieces back to ambient temperature over a period of approximately 36 hours.

9. The process according to claim 1 in which said first plate piece is cut into three pieces; said three pieces being brought into contact and mated to form an H shape.

* * * * *